US005514707A

United States Patent [19]
Deckelbaum et al.

[11] Patent Number: 5,514,707
[45] Date of Patent: May 7, 1996

[54] INHIBITION OF SMOOTH MUSCLE CELL PROLIFERATION BY 8-METHOXYPSORALEN PHOTOACTIVATED BY VISIBLE LIGHT

[75] Inventors: Lawrence I. Deckelbaum, Woodbridge; Francis P. Gasparro, Hamden; Bauer E. Sumpio, New Haven, all of Conn.

[73] Assignee: Yale University, New Haven, Conn.

[21] Appl. No.: 306,822

[22] Filed: Sep. 15, 1994

Related U.S. Application Data

[62] Division of Ser. No. 996,721, Dec. 24, 1992, Pat. No. 5,354,774.

[51] Int. Cl.$^6$ ................................................. A61K 31/35
[52] U.S. Cl. ........................................................ 514/455
[58] Field of Search ............................................. 514/455

[56] References Cited

U.S. PATENT DOCUMENTS

| | | | |
|---|---|---|---|
| 4,684,521 | 8/1987 | Edelson | 424/101 |
| 4,824,436 | 4/1989 | Wolinsky | 604/53 |
| 4,838,852 | 6/1989 | Edelson et al. | 604/4 |
| 4,878,492 | 11/1989 | Sinofsky et al. | 128/303.1 |
| 5,032,679 | 7/1991 | Brandley et al. | 536/21 |
| 5,042,980 | 8/1991 | Baker et al. | 606/7 |
| 5,114,721 | 5/1992 | Cohen et al. | 424/534 |
| 5,116,864 | 5/1992 | March et al. | 514/455 |
| 5,147,289 | 9/1992 | Edelson | 604/4 |

OTHER PUBLICATIONS

Edelson, R., "Photopheresis: A Clinically Relevant Immunobiologic Response Modifier," Annals of N.Y. Academy of Sciences 636:154–164 (1991).
Gasparro, F., et al., "Cell membrane DNA: a new target for psoralen photoadduct formation," Photochem. Photobiol. 52:315–321 (1990).
Cimino, G. D., et al., "Psoralens as photoactive probes of nucleic acid structure and function: organic chemistry, photochemistry, and biochemistry," Ann. Rev. Biochem. 54:1151–1193 (1985).
Kanne, D., et al., "Psoralen–deoxyribonucleic acid photoreaction. Characterization of the monoaddition products from 8-methoxypsoralen and 4,5', 8-trimethylpsoralen," Biochemistry 21:861–871 (1982).
Edelson, R., "Light-activated Drugs," Scientific American 256(8): 68–75 (1988).
Tessman, J. W., et al., "Photochemistry of the furan-side 8-methoxy-psoralen-thyamine monoadduct inside the DNA helix. Conversion to diadduct and to pyrone-side monoadduct," Biochemistry 24:1669–1676 (1985).
Spielmann, H., et al., "New Methods for the Large–Scale Synthesis of Furanside Psoralen Monoadducts and Diadducts," Photochem. Photo–biol. 53:1135 (1991).
Sastry, S., et al., "Recent advances in the synthesis and structure determination of site specific psoralen–modified DNA oligo–nucleotides," J. Photochem. Photobiol. B: Biol. 14:65–79 (1992).
Averbeck, D., "Mutagenesis by psoralens on eukaryotic cells," Photosensitization, ed. G. Moreno NATO ASI Series 15:279–291 (1988).
Averbeck D., "Recent advances in psoralen phototoxicity mechanism," Photochem. Photobiol. 50:859–882 (1989).
Sage, E., and Bredberg, A., "Damage distribution and mutation spectrum: the case of 8-methoxypsoralen plus UVA in mammalian cells," Mutation Research 263:217–222 (1991).
Cundari, E., Averbeck, D., "8-Methoxypsoralen-photoinduced DNA crosslinks as determined in yeast by alkaline step elution under different reirradiation conditions. Relation with genetic effects," Photochem. Photobiol. 48:315–320 (1988).
Bredberg, A. and Nachmansson, N., "Psoralen adducts in a shuttle vector plasmid propagated in primate cells: High mutagenicity of DNA cross–links," Carcinogenesis 8:1923–1927 (1987).
Edelson, R., et al., "Treatment of cutaneous T cell lymphoma by extracorporeal photochemotherapy," N. Engl. J. Med. 316:297–303 (1987).
Averbeck, D., et al., "Mutagenic and recombinogenic action of DNA monoadducts photoinduced by the bifunctional furocoumarin 8–Methoxypsoralen in yeast (*Saccharomyces cerevisiae*)," Photochem. Photobiol. 45:371–379 (1987).
Cassier, C., et al., "Mutagenic and recombinogenic effects of DNA cross–links induced in yeast by 8-methoxypsoralen photoaddition," Photochem. Photobiol. 39:799–803 (1984).
Singhal, R. P. et al., "High–performance liquid chromatography for trace analysis of DNA and kinetics of CNA modification," BioChrom. 4:78–88 (1989).
Malane, M. and Gasparro, R., "T Cell Molecular Targets for Psoralens," Annals of N.Y. Academy of Science 636:196–208 (1991).
Sage, E., and Moustacchi, E., "Sequence context effects on 8-methoxypsoralen photobinding to defined DNA fragments," Biochemistry 26:3307–3314 (1987).
Potapenko, A. Y., "Mechanisms of photodynamic effects of furocoumarins," J. Photochem. Photobiol. B 9:1–33 (1991).
Babudri, N., et al., "Mutation Induction and killing of V79 chinese hamster cells by 8-methoxypsoralen plus near–ultraviolet light: relative effects of monoadducts and crosslinks," Mutation Res. 91:391–394 (1981).

(List continued on next page.)

*Primary Examiner*—Raymond Henley, III
*Assistant Examiner*—Keith MacMillan
*Attorney, Agent, or Firm*—Wolf, Greenfield & Sacks

[57] ABSTRACT

A method for inhibiting smooth muscle cell proliferation in an injured blood vessel includes the steps of administering a photoactivatable psoralen to a patient in an amount to achieve local arterial tissue levels of psoralen suitable for light-dependent inhibition of smooth muscle cell growth, and delivering radiation in the visible wavelength range to the injured region of the blood vessel at a level sufficient for photoactivation of the psoralen. The psoralen is preferably 8-methoxypsoralen and can be delivered systemically or locally. The method of the invention can be used for preventing restenosis in a blood vessel following transluminal angioplasty. Both the psoralen and the visible light can be delivered with a laser balloon catheter having a porous balloon. The method of the invention may also be used for inhibiting proliferation of other undesired cell types in a patient's body.

6 Claims, 3 Drawing Sheets

OTHER PUBLICATIONS

Yang, et al., "8–MOP DNA Photoadducts in Patients Treated with 8–MOP and UVA," J. Invest. Dermatol. 92:59–63 (1989).

Deckelbaum, L., et al., "Inhibition of Smooth Muscle Cell Proliferation by 8–Methoxypsoralen Photoactivated by Visible Light," American Heart Assoc. 65th Scientific Session, abstract No. 135231 (1992).

Gasparro, F. P., et al., "Repair of 8–MOP photoadducts in human lymphocytes," DNA Damage and Repair in Human Tissues (eds. B. M. Sutherland and A. D. Woodhead) Plenum Press, NY, p. 137 (1990).

Bevilacqua, P. M., et al., "High performance liquid Chromatography analysis of 8–methoxypsoralen monoadducts and crosslinks in lymphocytes and keratinocytes," J. Invest. Dermatol. 97:151–155 (1991).

Gasparro, F. P., et al., "Rapid and sensitive analysis of 8–methoxypsoralen in plasma," J. Invest. Dermatol. 90:234–236 (1988).

Hosken, N. A., et al., "Class I–Restricted Presentation Occurs Without Internalization or Processing of Exogenous Antigenic Peptides," The Journal or Immunology, vol. 142:1079–1083 (Feb. 15, 1989).

Townsend, A. R. M., et al., "The Epitopes of Influenza Nucleoprotein Recognized by Cytotoxic T Lymphocytes Can be Defined with Short Synthetic Peptides," Cell, vol. 44:959–968 (Mar. 28, 1986).

Austin, G. E., et al., "Intimal Prolif. of Smooth Muscle Cells as an Expl. for Recurrent Coronary Artery Stenosis After Percutaneous Trans. Coronary Angio.", JACC, vol. 6, No. 2, Aug. 1985, pp. 369–375.

5,514,707

INHIBITION OF SMOOTH MUSCLE CELL PROLIFERATION BY 8-METHOXYPSORALEN PHOTOACTIVATED BY VISIBLE LIGHT

This application is a division of application Ser. No. 07/996,721 filed Dec. 24, 1992, now U.S. Pat. No. 5,354,774.

FIELD OF THE INVENTION

This invention relates to an improved method for preventing restenosis following transluminal angioplasty and, more particularly, to a method for inhibiting smooth muscle cell proliferation in a blood vessel.

BACKGROUND OF THE INVENTION

Balloon angioplasty has been utilized for a number of years to treat coronary arteries narrowed by plaque deposits. A catheter having an inflatable balloon secured to its distal end is advanced through an artery to a narrowed region. The balloon is then inflated with a fluid from an external source, causing the narrowed region of the artery to be expanded. The balloon is then deflated and withdrawn. Other transluminal angioplasty techniques have been proposed, including the use of laser energy to vaporize plaque deposits and the use of a heating element to melt and plow through plaque deposits.

A serious problem associated with angioplasty has been the occurrence in up to 30% of the cases of so-called restenosis, either immediately after the procedure or within six months. Evidence from various studies demonstrates that smooth muscle cell proliferation plays a major role in the intimal hyperplasia that occurs after angioplasty or vascular injury. See, for example, G. E. Austin et al, "Intimal Proliferation of Smooth Muscle Cells as an Explanation for Recurrent Coronary Artery Stenosis After Percutaneous Transluminal Coronary Angioplasty", *JACC*, Vol. 6, No. 2, August 1985, pages 369–375. Thus, inhibition of smooth muscle cell proliferation is expected to reduce neointima formation and the incidence of restenosis. Proposed techniques for inhibiting smooth muscle cell proliferation have involved administration of heparin and heparin derivatives. See, for example, U.S. Pat. No. 4,824,436 issued Apr. 25, 1989 to Wolinsky and U.S. Pat. No. 5,032,679 issued Jul. 16, 1991 to Brandley et al.

Another technique for inhibiting smooth muscle cell proliferation following vascular recanalization is disclosed in U.S. Pat. No. 5,116,864 issued May 26, 1992 to March et al. A photoactivatable psoralen is administered to a patient prior to a recanalization procedure. After recanalization of stenosed blood vessel, ultraviolet radiation is delivered to the recanalized region, causing the psoralen to be activated. The activated psoralen reportedly inhibits smooth muscle cell proliferation. The mechanism of the antiproliferative effect is postulated to be due to the formation of psoralen-DNA adducts that impair DNA translation and replication.

The use of ultraviolet radiation for activation of the psoralen has certain disadvantages. The construction of a catheter having an optical fiber and a diffusing tip for delivery of ultraviolet radiation is relatively difficult. Furthermore, the ultraviolet radiation has a relatively shallow penetration depth in the stenosed region of the blood vessel, whereas relatively deep penetration is desired to effectively inhibit smooth muscle cell proliferation. Finally, ultraviolet radiation is known to be mutagenic and cytotoxic when applied to human tissue.

S. Sastry et al, "Recent Advances in the Synthesis and Structure Determination of Site Specifically Psoralen-Modified DNA Oligonucleotides", *J. Photochem. Photobiol. B: Biol.*, Vol. 14, 1992, pages 65–79, describes activation of synthetic psoralen in a DNA solution at 406.7 and 413 nanometers. The synthetic psoralen compound (hydroxymethyl-psoralen) is not approved for clinical use. The DNA solution described by Sastry et al contained a relatively high concentration of the synthetic psoralen.

It is an object of the present invention to provide improved methods for photoactivation of psoralen when used to inhibit smooth muscle cell proliferation.

It is another object of the present invention to provide improved methods for prevention of restenosis following transluminal angioplasty.

It is a further object of the present invention to provide improved methods for inhibition of smooth muscle cell proliferation following transluminal angioplasty.

SUMMARY OF THE INVENTION

According to the present invention, these and other objects and advantages are achieved in a method for inhibiting smooth muscle cell proliferation in an injured blood vessel. The method comprises the steps of administrating a photoactivatable psoralen to a patient in an amount to achieve local arterial tissue levels of psoralen suitable for light-dependent inhibition of smooth muscle cell growth, and delivering radiation in the visible wavelength range to the injured region of the blood vessel at a level sufficient for photoactivation of the psoralen.

According to another aspect of the invention, a method for preventing restenosis in a blood vessel following transluminal angioplasty is provided. The method comprises the steps of administering a photoactivatable psoralen to a patient, the psoralen being administered in an amount to achieve local arterial tissue levels of psoralen suitable for light-dependent inhibition of smooth muscle cell growth, and delivering radiation in the visible wavelength range to the stenosed region of the blood vessel at a level sufficient for photoactivation of the psoralen.

The radiation used for photoactivation of the psoralen is in a wavelength range greater than about 400 nanometers and is preferably in a wavelength range equal to or greater than about 420 nanometers. The radiation in the visible wavelength range is easier to deliver to the stenosed region of the blood vessel, is deeper penetrating and is less mutagenic than ultraviolet radiation.

The psoralen is preferably 8-methoxypsoralen. The psoralen can be delivered systemically or locally.

In a preferred embodiment, a catheter having a porous balloon at or near its distal end is advanced to the stenosed region of the blood vessel, and the photoactivatable psoralen is delivered through the porous balloon to the stenosed region. The catheter preferably includes an optical fiber having a diffusing tip that is located within the porous balloon. Radiation in the visible wavelength range is delivered through the optical fiber to the diffusing tip such that the radiation passes through the porous balloon and irradiates the blood vessel, thereby activating the psoralen.

According to a further aspect of the invention, a method for inhibiting proliferation of undesired cells in a patients' body is provided. The method comprises the steps of administering a photoactivatable psoralen to a patient in an amount to achieve levels of psoralen in the undesired cells suitable for light-dependent inhibition of undesired cell proliferation, and delivering radiation in the visible wavelength range to the undesired cells at a level sufficient for photoactivation of the psoralen.

BRIEF DESCRIPTION OF THE DRAWINGS

For a better understanding of the present invention, together with other and further objects, advantages and capabilities thereof, reference is made to the accompanying drawings, which are incorporated herein by reference and in which.

DETAILED DESCRIPTION OF THE INVENTION

According to the present invention, a method for inhibiting smooth muscle cell proliferation in a blood vessel is provided. The method involves administrating a photoactivatable psoralen, such as 8-methoxypsoralen (8-MOP), to a patient so that the psoralen is taken up in the cells of the blood vessel to be treated. The psoralen is activated by visible light in a wavelength range greater than about 400 nanometers and is preferably activated by visible light in a wavelength range equal to or greater than about 420 nanometers. The activated psoralen inhibits smooth muscle cell proliferation in an injured or recanalized blood vessel.

The method for inhibiting smooth muscle cell proliferation in accordance with the invention is preferably utilized to prevent restenosis following transluminal angioplasty. A stenosed region of a blood vessel is recanalized utilizing any known recanalization technique. Examples include balloon angioplasty, laser angioplasty, laser balloon angioplasty and thermal angioplasty. A photoactivatable psoralen is administered to the patient either before or after the angioplasty procedure. After recanalization of the stenosed region of the blood vessel, visible light is delivered to the recanalized region in an amount sufficient to activate the psoralen. The activated psoralen inhibits smooth muscle cell proliferation in the recanalized region of the blood vessel. The preferred psoralen is 8-MOP.

As indicated above, the psoralen is activated with visible light in a wavelength range greater than about 400 nanometers and is preferably activated by visible light in a wavelength range equal to or greater than about 420 nanometers. As described below, a light source having a peak wavelength of 420 nanometers and a bandwidth of 34 nanometers has been used for irradiation of smooth muscle cell cultures in vitro. A proposed light source for activation of psoralen following transluminal angioplasty is a helium cadmium continuous wave laser having a wavelength of 442 nanometers. A dosage in the range of about 10 to 40 J/cm$^2$ is preferred. A continuous wave or low power pulsed light source can be used for practice of the present invention. Other suitable sources include a mode-locked argon laser and diode lasers.

Figure 1:
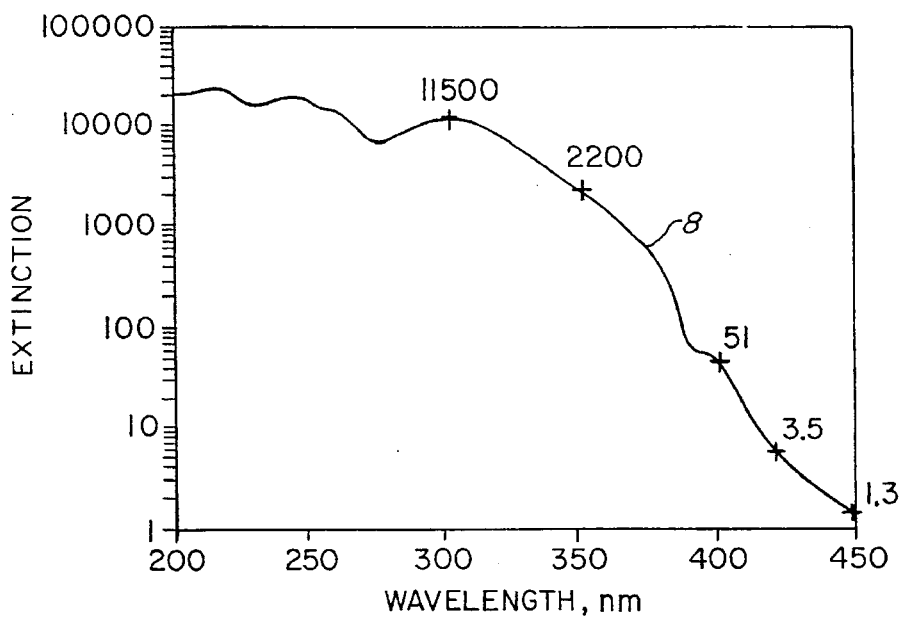
FIG. 1 is a graph of the extinction coefficient of 8-methoxypsoralen is a function of wavelength.

In the prior art, it has long been accepted that 8-MOP is most efficiently activated by ultraviolet radiation. This practice was based on the absorption spectrum of 8-MOP, as shown in FIG. 1. The extinction coefficient of 8-MOP (curve 8) is plotted as a function of wavelength on a logarithmic scale. FIG. 1 shows that the absorption of 8-MOP is greatly reduced in visible wavelength range as compared with the ultraviolet wavelength range. We have discovered that the effectiveness of inhibition of smooth muscle cell proliferation produced by photoactivation of 8-MOP with visible light is approximately 2 to 3 orders of magnitude greater than would be expected from the absorption characteristic shown in FIG. 1. Furthermore, visible light is easier to deliver, deeper penetrating in tissue, less mutagenic and less cytotoxic than ultraviolet radiation.

The primary effect of using visible light instead of long wavelength ultraviolet radiation for photoactivation of 8-MOP is a more than tenfold reduction in the extent of crosslink formation. The significance of favoring monoadduct formation over crosslink formation in accordance with the present invention is that the procedure is less cytotoxic and less mutagenic than prior art techniques which use ultraviolet radiation. Furthermore, the monoadducts may be easier to repair than crosslinks, and better cell recovery occurs.

The psoralen can be administered systemically or locally. A technique for intraarterial delivery of the psoralen is described below. As indicated above, 8-MOP is preferred for inhibition of smooth muscle cell proliferation. Other suitable psoralens include 5-methoxypsoralen and amino-methyl trimethylpsoralen. The effect on smooth muscle cell proliferation is presumed to be proportional to the product of drug dose and light dose. Thus, when a higher drug dose is utilized, a lower light dose may be utilized, and vice versa. Psoralen doses for in vitro studies described below were on the order of 1050 nanograms per milliliter of 8-MOP. In general, it is expected that higher doses will be required for in vivo practice of the invention.

Figure 2:
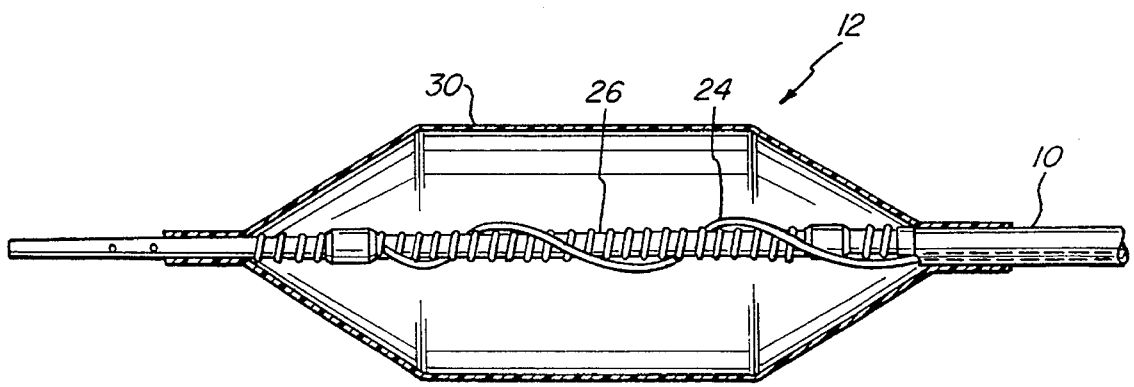
FIG. 2 is a schematic representation of the distal end of a catheter suitable for practice of the present invention.

A preferred technique for practicing the present invention is described with reference to FIG. 2. The distal end of a catheter for delivering a photoactivatable psoralen intraarterially and for delivering visible light for activation of the psoralen is shown in FIG. 2. An elongated flexible tube 10 has a balloon assembly 12 at its distal end. The balloon assembly 12 includes an optical fiber diffusing tip 24 for emitting laser radiation, a central shaft 26 adapted for carrying a guidewire, and a porous balloon 30 which is inflated and deflated from the proximal end of the flexible tube 10. An optical fiber extends through a lumen of the flexible tube 10 and terminates in the optical fiber diffusing tip 24. Further details regarding the construction of a laser balloon catheter similar to that shown in FIG. 2 are disclosed in U.S. Pat. No. 4,878,492 issued Nov. 22, 1989 to Sinofsky et al, which is hereby incorporated by reference.

In use, the catheter carrying the balloon assembly 12 is advanced through a blood vessel to a recanalized region. The balloon is inflated with a fluid containing the photoactivatable psoralen. The inflated balloon displaces blood in the vessel. The pores in the balloon allow the psoralen to pass from the balloon into the vessel wall. When a sufficient quantity of psoralen has been delivered to the vessel wall, visible light energy is delivered through the optical fiber to the diffusing tip. The light energy passes through the balloon wall in a circumferential pattern and activates the psoralen in the blood vessel, thereby inhibiting smooth muscle cell proliferation. The balloon is then deflated and the catheter is withdrawn from the vessel. Alternatively, the psoralen can be delivered using any catheter designed for intraarterial drug delivery.

A dose response study was performed to evaluate the effects of visible light activated 8-MOP on smooth muscle cell proliferation in vitro. Sub-confluent cultures of bovine aortic smooth muscle cells were incubated in the dark for 30 minutes with 1050 nanograms per milliliter 8-MOP and then irradiated with a broadband blue light source. The light source had a peak wavelength of 420 nanometers, a bandwidth of 34 nanometers, and an irradiates of 6.4 milliwatts/square centimeter. Treated cultures received a radiant exposure ranging from 2 to 69 joules/square centimeter ($J/cm^2$). Following irradiation, cells were washed and fresh media was added. Control smooth muscle cells were not treated with visible light or 8-MOP. An additional group of 8-MOP treated cells was irradiated with 2 $J/cm^2$ ultraviolet UVA radiation for comparison. The cell number was assessed at Day 3 using a Coulter counter and compared to the Day 0 baseline.

Figure 3:
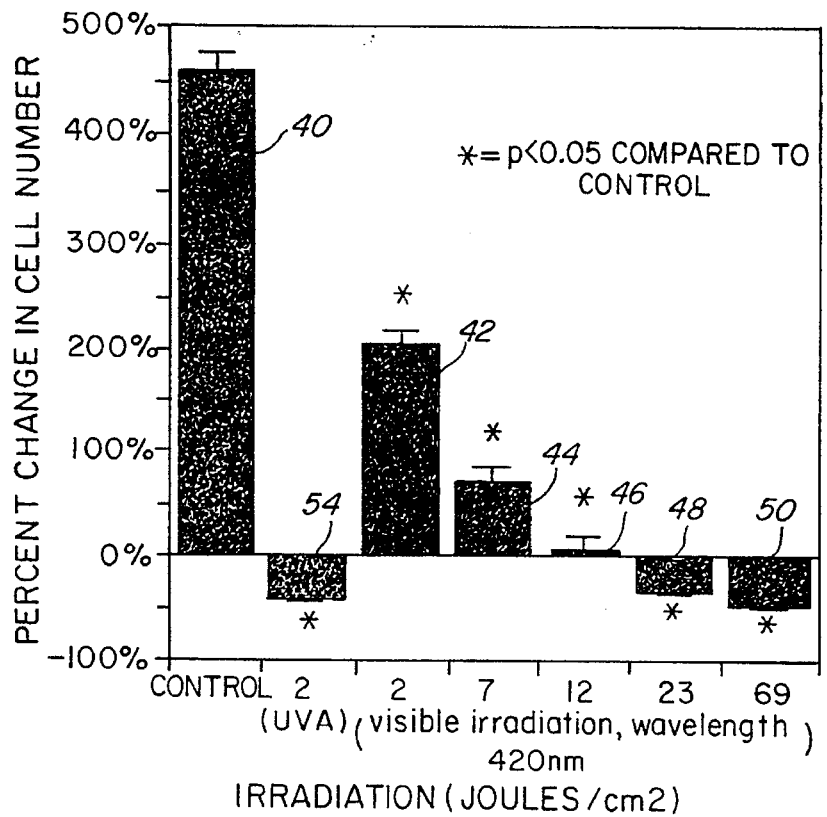
FIG. 3 is a bar graph that shows the percent change in smooth muscle cell number for different treatment regimens.

The bar graph of FIG. 3 shows the dose response of smooth cell proliferation in response to visible light irradiation and 8-MOP. The mean and standard error of the change in cell number at Day 3 relative to Day 0 is plotted as a function of the treatment regimen. Cell number in the control smooth muscle cell cultures, shown by bar 40, increased 458% over the three days. In contrast, smooth muscle cells treated with 8-MOP and visible light, shown by bars 42, 44, 46, 48 and 50, demonstrated a dose dependent inhibition of proliferation. The highest doses of 23 and 69 $J/cm^2$ resulted in cell toxicity, with a decrease in cell number of 36% and 50%, respectively. The lowest light doses of 2 and 7 $J/cm^2$ resulted in reduced proliferation, with a three day cell number increase of 199% and 67%, respectively. A visible light dose of 12 $J/cm^2$ resulted in minimal cell proliferation, with only a 5% increase in cell number. Inhibition of proliferation at these lower light doses occurred without cidal effect, as demonstrated by trypan blue exclusion. In comparison to the mild inhibition of proliferation at 2 $J/cm^2$ visible light irradiation, ultraviolet UVA irradiation at 2 $J/cm^2$, shown by bar 54, resulted in cell toxicity, with a decrease in cell number of 43%.

To evaluate the time course and duration of smooth muscle cell proliferation, sub-confluent smooth muscle cell cultures were incubated with 1050 nanograms per milliliter 8-MOP and then irradiated with 7–12 $J/cm^2$ visible light at 420 nanometers. Serial cell counting was performed at 2–4 day intervals over the subsequent 5–14 days. Control cell cultures were treated with 8-MOP alone, light alone, or neither.

Figure 4:
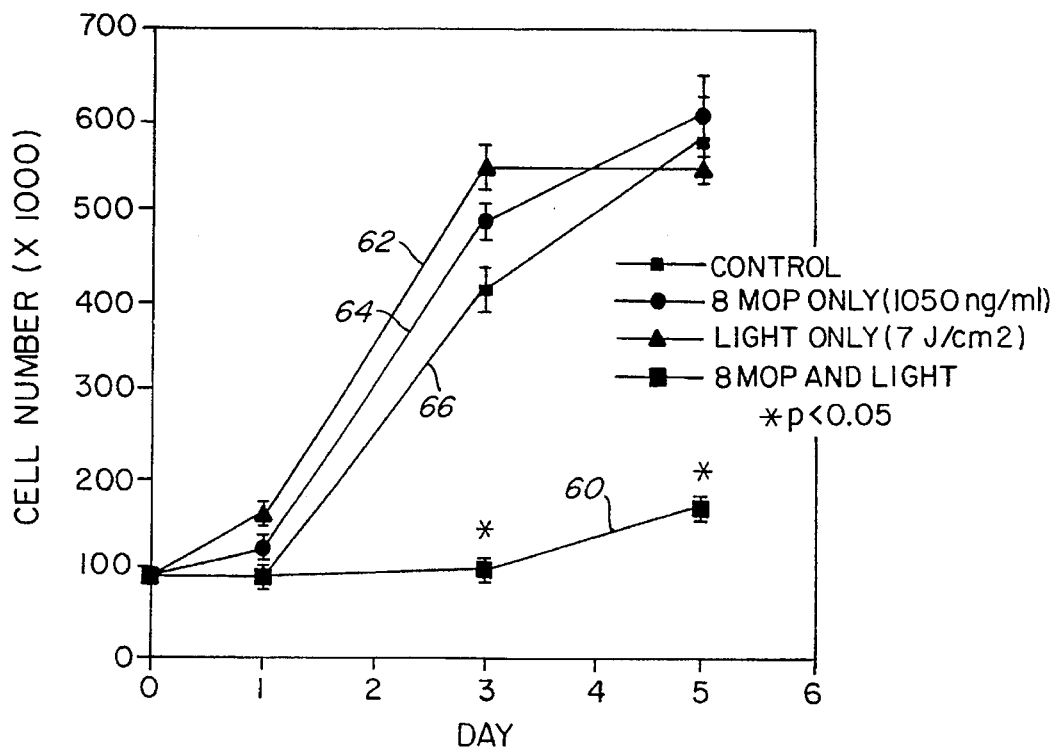
FIG. 4 is a graph that shows the 5 day time course of the change in smooth muscle cell proliferation for different treatment regimens.

The 5 day time course of the change in smooth muscle cell number is shown in FIG. 4. The result for a cells treated with 8-MOP and visible light is shown by curve 60. The result for cells treated with visible light alone is shown by curve 62. The result for cells treated with 8-MOP alone is shown by curve 64. The result for cells treated with neither light nor 8-MOP is shown by curve 66. It can be seen that inhibition of smooth muscle cell proliferation occurs only when the cells were treated with both light and 8-MOP. Neither light nor 8-MOP alone had any inhibitory effect. Following treatment with 8-MOP and 7 $J/cm^2$ visible light, the cell number was stable through day 3, but began to increase at Day 5.

Figure 5:
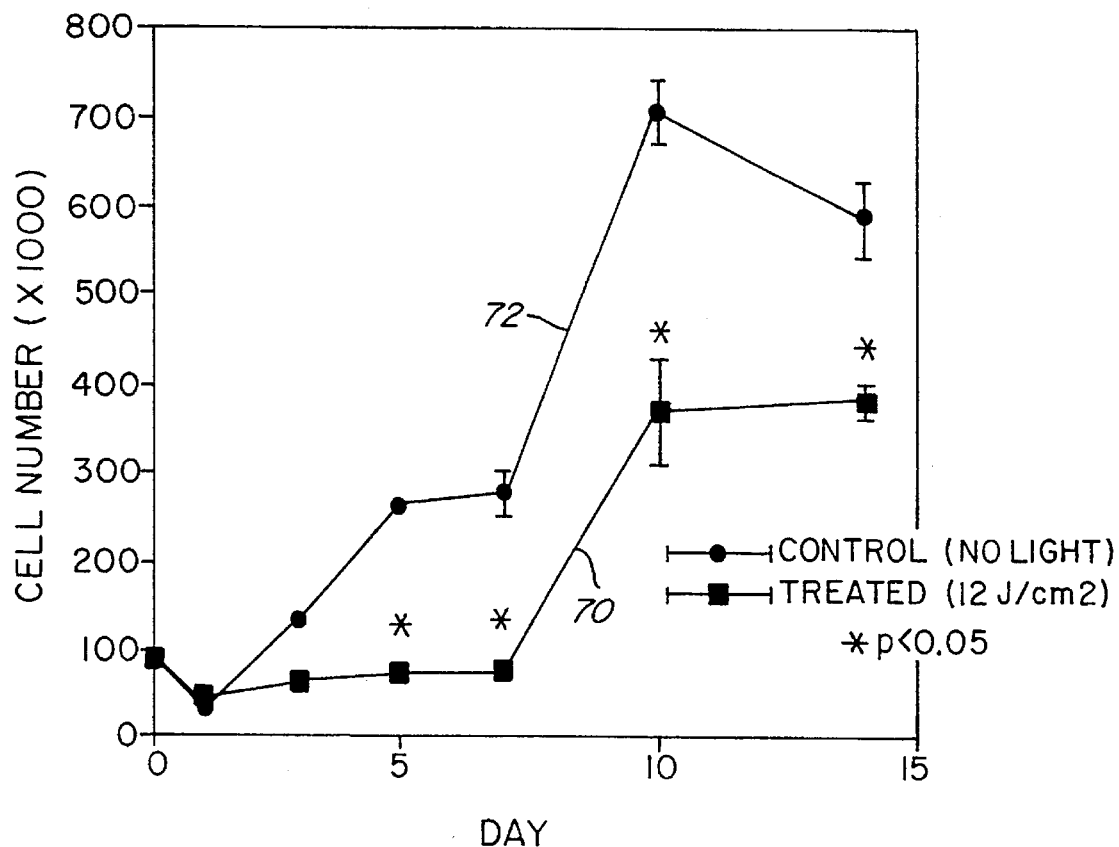
FIG. 5 is a graph that shows the 14 day time course of the change in smooth muscle cell proliferation for different treatment regimens.

To investigate whether inhibition of proliferation could be prolonged, a higher light dose was evaluated. The 14 day time course of the change in smooth muscle cell number is shown in the graph of FIG. 5. The change in smooth muscle cell number for cells treated with 8-MOP and a dose of 12 $J/cm^2$ visible light at 420 nanometers is indicated by curve 70. The change in smooth muscle cell number for control cells treated with 8-MOP alone is indicated by curve 72. Compared to 7 $J/cm^2$ (curve 60 in FIG. 4), treatment with 12 $J/cm^2$ visible light resulted in a longer period of inhibition of cell proliferation, as evidenced by the constant cell number over 7 days. Cell proliferation resumed after Day 7, as reflected by the increase in cell number at Day 10.

To determine photoadduct formation, smooth muscle cells were incubated with tritiated 8-MOP and irradiated with 7–12 $J/cm^2$ visible light at 420 nanometers. The cells were then washed to remove unbound 8-MOP and detached from the dish by trypsinization. DNA was isolated from the cells and the extent of photoadduct formation was calculated from the incorporated radioactivity. The DNA was then enzymatically hydrolyzed and analyzed by reversed phase high performance liquid chromatography. The relative numbers of crosslinks and monoadducts were determined from the radioactivity of each eluted fraction. For comparison, photoadducts were also evaluated from 8-MOP treated smooth muscle cells irradiated with 2 $J/cm^2$ ultraviolet UVA radiation.

Table I below shows the results of the quantization of photoadduct formation after 420 nanometer irradiation of smooth muscle cells treated with 1050 nanograms per milliliter 8-MOP. Over the range of 7–12 $J/cm^2$, there was a dose dependent increase in the number adducts formed per megabase pair. At 7 $J/cm^2$, 9.8 adducts were formed, whereas at 12 $J/cm^2$, 14 4 adducts were formed. As can be seen by the distribution of adducts, approximately 95% of the adducts formed were monoadducts. In contrast, following radiation with 2 $J/cm^2$ ultraviolet UVA radiation, a greater number of adducts was formed, 88 per megabase pair. However, almost half the adducts formed were crosslinks. This greater percent crosslink formation may partly account for the observed greater cytotoxicity observed following ultraviolet radiation as compared to visible irradiation of 8-MOP treated cells.

TABLE I

| PHOTOADDUCT FORMATION IN SMOOTH MUSCLE CELLS (1050 ng/ml 8-MOP) | | | |
|---|---|---|---|
| | visible 420 nm | | UVA |
| | 7 $J/cm^2$ | 12 $J/cm^2$ | 2 $J/cm^2$ |
| number per million DNA base pairs: | 9.8 | 14.4 | 88 |
| distribution of adducts: | | | |
| crosslinks | 3% | 9% | 47% |
| monoadducts | 97% | 91% | 53% |

In summary, visible light and 8-MOP therapy inhibited smooth muscle cell proliferation in a dose dependent fashion. Cell toxicity was evident at 3 days following light doses greater than or equal to 23 $J/cm^2$, whereas an absence or reduction of proliferation was evident at doses less than or equal to 12 $J/cm^2$. Both light and 8-MOP were required to inhibit cell proliferation. Inhibition of proliferation following a single dose of 8-MOP and 12 $J/cm^2$ visible light persisted for 7 days. Inhibition was reversible, and cell number increased by Day 10.

The inhibition of cell proliferation by psoralen photoactivated with visible light in accordance with the invention may also be useful for inhibiting proliferation of other undesired cell types, such as tumor cells and inflammatory cells. The technique of the invention is not necessarily catheter based, as described above, but depends on the location of the cells to be treated.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for inhibiting smooth muscle cell proliferation in an injured blood vessel, comprising the steps of:

administering a photoactivatable psoralen to a patient in an amount to achieve arterial tissue levels of psoralen suitable for light-dependent inhibition of smooth muscle cell growth; and delivering radiation in the visible wavelength range equal to or greater than about 420 nanometers to the injured region of the blood vessel at a level sufficient for photoactivation of the psoralen.

2. A method as defined in claim 1 wherein the psoralen comprises 8-methoxypsoralen.

3. A method as defined in claim 2 wherein the 8-methoxypsoralen is administered systemically.

4. A method as defined in claim 2 wherein the 8-methoxypsoralen is administered locally.

5. A method as defined in claim 2 wherein the radiation is delivered at a dose in the range of about 10 to 40 $J/cm^2$.

6. A method for inhibiting proliferation of undesired cells in a patients' body, comprising the steps of:

administering a photoactivatable psoralen to a patient in an amount to achieve levels of psoralen in the undesired cells suitable for light-dependent inhibition of undesired cell proliferation; and delivering radiation in the visible wavelength range equal to or greater than about 420 nanometers to the undesired cells at a level sufficient for photoactivation of the psoralen.

* * * * *